United States Patent [19]

Kawahara et al.

[11] Patent Number: 4,689,080
[45] Date of Patent: Aug. 25, 1987

[54] BASE MATERIAL COMPOSITION FOR DENTAL TREATMENT

[75] Inventors: Haruyuki Kawahara, 28 Toko-cho 1-chome, Moriguchi-shi; Shoji Takeda, Ibaragi, both of Japan

[73] Assignee: Haruyuki Kawahara, Moriguchi, Japan

[21] Appl. No.: 910,334

[22] Filed: Sep. 19, 1986

Related U.S. Application Data

[63] Continuation of Ser. No. 758,831, Jul. 24, 1985, abandoned, which is a continuation of Ser. No. 524,524, Aug. 17, 1983, abandoned.

[51] Int. Cl.$^4$ ............................................. C08K 7/14
[52] U.S. Cl. ........................................ 106/35; 106/85; 501/153
[58] Field of Search ................. 501/153; 106/35, 85

[56] References Cited

U.S. PATENT DOCUMENTS

| | | | |
|---|---|---|---|
| 1,507,379 | 9/1924 | Hoskins | 106/85 |
| 1,671,104 | 5/1928 | Eberly | 106/35 |
| 2,036,728 | 4/1936 | Simon | 106/35 |
| 2,304,391 | 12/1942 | Zimmerman | 106/85 |
| 2,941,890 | 6/1960 | Mandberg | 106/35 |
| 3,649,732 | 3/1972 | Brigham et al. | 106/85 |
| 3,787,900 | 1/1974 | McGee | 106/35 X |
| 4,123,416 | 10/1978 | Potter et al. | 106/35 X |
| 4,311,528 | 1/1982 | Dietz et al. | 106/35 |

FOREIGN PATENT DOCUMENTS

| | | | |
|---|---|---|---|
| 0134407 | 8/1982 | Japan | 106/35 |
| 0099406 | 6/1983 | Japan | 106/35 |

*Primary Examiner*—Nancy A. Swisher
*Attorney, Agent, or Firm*—Koda and Androlia

[57] ABSTRACT

This invention relates to a base material composition for dental treatment comprising 100 parts by weight of alumina cement powder, 1–50 parts by weight of calcium type powder hardening retarder, and 1–20 parts by weight of hardening retarder for restraining dispersion of calcium ion. This composition has appropriate hardening time and consistency, and is higher in strength and lower in solubility. The composition gets hardened by low alkalinity and is very low in tissue irritation.

32 Claims, No Drawings

BASE MATERIAL COMPOSITION FOR DENTAL TREATMENT

This is a continuation of application Ser. No. 758,831 filed July 24, 1985 now abandoned which in turn is a continuation of application Ser. No. 524,524 filed Aug. 17, 1983, now abandoned.

BACKGROUND OF THE INVENTION

1. Field of the Invention

This invention relates to a base material composition for use in dental treatment and more particularly to a base material composition mainly comprising alumina cement and which is fit for use in dental pulp capping materials, canal filling materials, sealing agents, alveolar bone reconstruction materials and the like.

2. Prior Art

In the field of dental treatment, various materials are used as a canal filling or capping material. The canal filling material heals an infected canal by blocking the pulp cavity after the pulp tissue has been lost. The canal capping material protects the dental pulp in the case of cavity preparation. However, the fact is that there has so far been no satisfactory material available.

A description will now be given of the materials described above with reference to a canal filling material as an example. The most desirable canal filling material generally includes non-irritation, non-toxicity, affinity with tissue and adaptability to canal walls, antibacterial effects or healing effects, high strength, unchangeability in volume, insolubility in tissue fluid, removable and recurable properties, contrasting property, ease of handling and the like. With respect to the contrasting property mentioned above, mixing of a suitable contrast medium into the material may make desirable filling material, however, conditions greatly depend upon the properties of the base material itself of the canal filling material.

For example, one of the typical canal filling materials used widely today is a base material of a zinc oxide eugenol type. However, since this is an acidic material, it has an irritating property and has no healing effect. Another typical example of a canal filling material is one which is used in a base material of a calcium hydroxide type. However, since this is low in strength and is a strong alkaline material, it may deteriorate the tissue. The calcium hydroxide type material is likely to gradually convert into a calcium carbonate. Besides, although a formaldehyde type base material or an iodoform type based material are used as a canal filling material, such filling material has both merits and demerits. In this manner, there has been developed no materials which satisfy the above conditions.

SUMMARY OF THE INVENTION

This invention has been made in view of the above circumstances.

The inventor has noticed the use of industrial alumina cement which no one concerned with dentistry expected, for the purpose of dental treatment and has successfully improved the applicability of industrial alumina cement to a base material for use in dental treatment after various studies.

DETAILED DESCRIPTION OF THE INVENTION

This invention relates to a base material composition for dental treatment comprising alumina cement powder, calcium type powder hardener mixed with the alumina cement powder in a ratio of 1–50 parts by weight of the former to 100 parts by weight of the latter, and 1–20 parts by weight of hardening retarder which restrains the dispersion of calcium ion.

The composition of the invention is characterized in that the composition is hardened in its low alkaline state in the above range of composition, and that the composition is slightly inferior in strength to the conventional dental cement itself but is sufficient as a base material (superior to conventional capping materials). Accordingly, the composition of the invention has in a single unit three functions in combination:

A capping material at the bottom layer: a material designed to prevent adverse effects of medication from the filling material side on the dental pulp.

A lining material at the middle layer: a material designed to prevent adverse effects of medication from the inside of the oral cavity and from the filling material side on the capping material.

A base material at the top layer: a rigid member designed to sufficiently resist biting force.

Furthermore, when a resin type prosthetic material is applied to a tooth or teeth in the future, the composition is advantageous in that it produces no chemical ill effects upon the polymerization of the resin material.

The alumina cement powder forming a main ingredient of the composition of the invention consists of calcium aluminate ($CaO.Al_2O_3$) containing about 80% by weight of aluminum oxide and about 20% by weight of calcium oxide in a ratio of the former to the latter. The cement powder identified above is being commercially available in the form of industrial cement at low prices.

The calcium type powder hardener used in the invention includes calcium hydroxide, calcium chloride, calcium oxide and the like, and calcium hydroxide powder is particularly suitable for use in the hardener. Such a calcium type powder hardener, as described above, must have the ratio of 1–50. Parts by weight to 100 parts by weight of alumina cement. The reason is that since the use of the hardener in the amount not exceeding one part by weight needs longer period of time for hardening the compsoition and the strength of the composition lowers, the composition becomes not suitable for a base material for use in a dental pulp capping material and a canal filling material. Further, when more thah 50 parts by weight of hardener is used, the hardening speed increases and alkalinity becomes higher, and the handling expediency and healing effect decrease. When hardening time, strength, healing effect and the like are taken into consideration, the use of the calcium type powder hardener in a ratio of about 20 parts by weight to alumina cement will bring the best results. With such ratios, a composition which is high in strength, great in healing effect and excellent in handling expediency is obtainable.

On the other hand, the hardening retarder used in this invention includes polyvinyl alcohol, polyvinyl pyrolidone, gum arabic, acrylic acid, glycerine, sodium metasilicate, low-molecular fatty acid, hydrophobic natural resin and the like, which are all capable of retarding dispersion of calcium ion conducive to hardening of alumina cement. The materials mentioned above are used in a single or a mixed manner. It is desirable that such hardening retarder be prepared in a ratio of 1–20 parts by weight of the retarder to 100 parts by weight of alumina cement powder. If the content of retarder does not exceed one part by weight, the hardening retarder does not provide sufficient effect, resulting in that the composition comes to get hardened in a very short time. On the contrary, if the retarder exceeds 20 parts by weight in content, the hardening effect exceeds the proper level, resulting in a longer hardening time. Either of the above effects is improper for a composition of a base material for dental treatment.

The composition according to the invention uses as its essential ingredients the above alumina cement powder, calcium type powder hardener, and hardening retarder. If, required, a filling agent such as titanium oxide powder and aluminum oxide powder may be added to increase strength. Addition of an antiseptic such as iodoform, poraformaldehyde or addition of various known contrast mediums and anti-inflammatory agents are not objectionable. With respect to percentage of addition of such secondary ingredients, there is no particular restriction to the percentage, and it may be determined as it is desired.

The composition of the invention may be classified into four types in accordance with the preservation manner prior to the use.

The first type is a powder-liquid type composition which preserves a mixed powder containing at least an alumina cement powder and a calcium type powder hardener separately from a liquid having at least a hardening retarder dissolved or dispersed in water. The second type is a powder-paste type composition which preserves separately the powder containing at least alumina cement powder from a paste obtained by adding a calcium type powder hardener to a solution or dispersing solution and kneading the mixture. The third type is a paste-liquid composition which preserves a paste prepared by adding at least alumina cement powder and a calcium type hardener to glycerine or the like and kneading the mixture separately from a liquid prepared by dissolving or dispersing at least a hardening retarder therein. The fourth type is a paste-paste type composition which separately preserves a paste prepared by adding at least alumina cement powder to glycerine or the like and kneading the mixture from a paste prepared by adding at lease a calcium type powder hardener to a calcium type powder hardening retarder solution or dispersing solution and kneading the mixture.

When the aforestated secondary ingredient, for example, a powder-liquid type composition, is added, it is only necessary to add a filling agent or the like to the powder and add previously an antiseptic, anti-inflammatory agent or the like to the liquid. In other words, it is preferable to add the second ingredient beforehand to one or both preservation types, i.e. powder or liquid or both types in this case, constituting the composition, or to knead both preservation types and, when used, add the secondary ingredient thereto.

The composition of base material for dental treatment according to the invention, as described above, is a powder material whose main ingredient is an alumina cement powder, and is adapted to provide proper alkalinity in use by bringing a calcium type powder hardener into a ratio of 1–50 parts by weight of the hardener to 100 parts by weight of the cement powder. Accordingly when the composition is used as a canal filling agent and a dental pulp capping agent, the antiseptic and healing effects due to this suitable alkaline property are brought into full swing, and hydrated gel composition is produced on the surface of the composition used. As a result, excellent adaptability to the canal walls and cavity walls and excellent affinity to the tissue are secured. When the hardening retarder, as described, is used in a ratio of 1–20 parts by weight or the retarder to 100 parts by weight of alumina cement powder, a composition easy to handle and requiring about several ten minutes for hardening is obtained. In addition, the composition of the invention has little or no toxicity or irritation, and the hardening substance in the invention is not only very high in strength with no change in volume but also insoluble into the tissue liquid and very high in durability. In addition, the composition causes no chemical ill effects upon the polymerization of normal-temperature polymerizable resin for dental treatment. Since the composition is excellent in removability, it readily permits retreatment. The advantages described above render the composition of the invention highly satisfactory as a base material for dental treatment.

A description will now be given more specifically for the composition of the invention with reference to the embodiments thereof.

EXAMPLE 1

To 100 wt parts of alumina cement powder (Al$_2$O$_3$:80wt %, CaO: 20 wt %) commercially available was added to 20 wt parts of calcium hydroxide and was mixed for two hours in a porcelain crucible to prepare mixed powder. Thereafter, 4 wt %, 6 wt %, 8 wt % and 10 wt % of aqueous solution of polyvinyl alcohol were prepared in four different concentrations to obtain a powder-liquid type composition.

Thereafter, to the resulting mixed preparation was added and kneaded each aqueous solution in percentages shown in the following Table 1, and measurement was made of each kneaded composition in conjunction with a hardening time, viscosity, solubility, pH change, compressive strength, and tissue irritability. The results obtained are also shown in the Table 1. (Note): The measurement was carried out in the following manner.

Hardening time: ADAS (American Dental Association Standard)-No. 16
Consistency: ADAS - No. 16
Solubility: ADAS - No. 8
pH change: A method similar to that of measuring solubility. ("199" means "tissue medium 199")
Compressive strength: ADAS - No. 8
Tissue irritability: Tissue culture method

TABLE 1

| | Powder<br>Alumina cement powder + 20 wt % Ca (OH)$_2$ | | | | | | | | | | | |
|---|---|---|---|---|---|---|---|---|---|---|---|---|
| | Liquid | | | | | | | | | | | |
| | 4 wt % PVA<br>aqueous<br>solution | | | 6 wt % PVA<br>aqueous<br>solution | | | 8 wt % PVA<br>aqueous<br>solution | | | 10 wt % PVA<br>aqueous<br>solution | | |
| Compounding ratio | 0.4 | 0.5 | 0.6 | 0.4 | 0.5 | 0.6 | 0.4 | 0.5 | 0.6 | 0.5 | 0.6 | 0.7 | 0.8 |

TABLE 1-continued

Powder
Alumina cement powder + 20 wt % Ca (OH)$_2$
Liquid

|  | 4 wt % PVA aqueous solution | | | 6 wt % PVA aqueous solution | | | 8 wt % PVA aqueous solution | | | 10 wt % PVA aqueous solution | | | |
| --- | --- | --- | --- | --- | --- | --- | --- | --- | --- | --- | --- | --- | --- |
| (ml/g) | | | | | | | | | | | | | |
| Hardening time | 5'30" | 11' | 18'30" | 5'30" | 10'30" | 16'30" | 4' | 8' | 11'30" | 3'30" | 8'30" | 14' | 20' |
| Consistency (mm) | 40 | 46 | 50 | 29 | 38 | 46 | 18 | 28 | 40 | 20 | 25 | 31 | 37 |
| Solubility (%) | | | | | | | | | | | | | |
| 24 hr in water | 4% | 4.9% | — | 42% | 5.1% | — | 4.2% | 4.9% | — | 3.9% | 4.3% | 4.8% | — |
| 1 week in water | 6.2 | 7.1 | — | 6.7 | 7.2 | — | 6.8 | 8.1 | — | 6.5 | 7.1 | 8.3 | — |
| 24 hr in 199 | 3.7 | 4.5 | — | 2.9 | 4.1 | — | 2.9 | 3.4 | — | 2.9 | 3.5 | 3.9 | — |
| 1 week in 199 | 4.9 | 5.8 | — | 4.8 | 5.9 | — | 5.2 | 5.9 | — | 4.4 | 4.9 | 6.5 | — |
| pH change | | | | | | | | | | | | | |
| In water | 11.6 | 11.6 | 11.6 | 11.6 | 11.5 | 11.6 | 11.6 | 11.5 | 11.6 | 11.5 | 11.6 | 11.5 | 11.6 |
| In 199 | 11.1 | 11.0 | 11.0 | 11.1 | 11.0 | 10.8 | 11.3 | 10.9 | 11.1 | 10.8 | 10.9 | 10.7 | 10.6 |
| Compression strength (Kg/cm$^2$) | 231 | 130 | 77 | 210 | 126 | 77 | 206 | 128 | 74 | 76 | 58 | 38 | 26 |
| Tissue irritability | | | | | | | | | | | | | |
| unset | ++ | ++ | ++ | ++ | ++ | ++ | ++ | ++ | ++ | ++ | ++ | ++ | ++ |
| set | + | + | + | + | + | + | + | + | + | + | + | + | + |

EXAMPLE 2

To each of 6 wt parts, 8 wt parts, and 10 wt parts of polyvinyl alcohol aqueous solution prepared in Example 1 was added 50 wt parts of titanium oxide. The mixture thus obtained was added to the mixed powder prepared in Example 1 and was kneaded in the compounding ratio shown in Table 2. The measurement was the same as that of Example 1. The results are additionally shown in Table 2.

TABLE 2

Powder
Alumina cement powder + 20 wt % Ca (OH)$_2$
Paste

|  | 6 wt % PVA aqueous solution + 50 wt % TiO$_2$ | | | | 8 wt % PVA aqueous solution + 50 wt % TiO$_2$ | | | | 10 wt % PVA aqueous solution + 50 wt % TiO$_2$ | | | |
| --- | --- | --- | --- | --- | --- | --- | --- | --- | --- | --- | --- | --- |
| Compounding ratio (ml/g) | 0.5 | 0.75 | 1.0 | 1.25 | 0.5 | 0.75 | 1.0 | 1.25 | 0.75 | 1.0 | 1.25 | 1.5 |
| Hardening time | 9'0" | 11'30" | 13'30" | 16'30" | 3'0" | 6'0" | 9'0" | 13'0" | 5'30" | 8'0" | 10'0" | 12'0" |
| Consistency (mm) | 21 | 33 | 40 | 42 | 18 | 25 | 34 | 40 | 20 | 24 | 29 | 36 |
| solubility (%) | | | | | | | | | | | | |
| 24 hr in water | 3.1% | 4.0 | 5.1 | — | 2.7 | 3.9 | 4.7 | — | 4.3 | 5.3 | 6.1 | — |
| 1 week in water | 3.9 | 4.7 | 6.0 | — | 5.3 | 6.6 | 7.3 | — | 5.7 | 6.3 | 8.4 | — |
| 24 hr in 199 | 3.7 | 4.8 | 6.2 | — | 3.4 | 5.0 | 5.5 | — | 4.6 | 5.0 | 5.8 | — |
| 1 week in 199 | 6.4 | 7.7 | 8.9 | — | 5.5 | 7.5 | 9.9 | — | 6.4 | 7.1 | 8.0 | — |
| pH change | | | | | | | | | | | | |
| In water | 11.6 | 11.6 | 11.6 | 11.6 | 11.5 | 11.6 | 11.6 | 11.7 | 11.6 | 11.7 | 11.6 | 11.6 |
| In 199 | 10.4 | 10.9 | 10.5 | 10.4 | 10.5 | 10.8 | 10.6 | 10.4 | 10.4 | 10.4 | 10.4 | 10.5 |
| Compression strength (Kg/cm$^2$) | 287 | 133 | 62 | 39 | 229 | 88 | 72 | 39 | 129 | 59 | 43 | — |
| Tissue irritability | | | | | | | | | | | | |
| unset | ++ | ++ | ++ | ++ | ++ | ++ | ++ | ++ | ++ | ++ | ++ | ++ |
| set | + | + | + | + | + | + | + | + | + | + | + | + |

EXAMPLE 3

Except that, instead of polyvinyl alcohol, polyvinylpyrrolidone or gum arabic was used as a hardening retarder, the same procedure as that in Example 1 was taken to obtain powder-liquid type compositions, and each of the compositions was measured. The results obtained are shown in Table 3. The measured values in Table 3 are not all the values enumerated one by one but are the minimum and maximum values.

TABLE 3

Powder
Same as in Example 1
Liquid

|  | Aqueous solution of 4–10 wt % polyvinyl pyrolidone | Aqueous solution of 4–10 wt % gum arabic |
| --- | --- | --- |
| Compounding ratio | Same as in Example 1 | Same as in Example 1 |
| Hardening time (min) | 2–20' | 5–25' |
| Consistency | 20–50 | 20–50 |
| pH change | | |
| Solubility (%) | | |
| 24 hr in water (%) | 4–6 | 4–6 |
| 24 hr in 199 (%) | 3–6 | 5–7 |

TABLE 3-continued

| | Powder Same as in Example 1 | |
|---|---|---|
| | Liquid | |
| | Aqueous solution of 4-10 wt % polyvinyl pyrolidone | Aqueous solution of 4-10 wt % gum arabic |
| in water | 11.4-11.7 | 11.4-11.7 |
| In 199 | 10.5-11.1 | 10.5-11.2 |
| Compression strength (Kg/cm²) | 20-200 | 15-210 |
| Tissue irritability | | |
| Unset | ++ | ++ |
| set | + | + |

As described above, it is apparent from the results in each Example that the compositions of the invention are very useful compositions having adequate hardening time and consistency. The compositions are also high in strength and small in solubility, suitable in pH value and very low in tissue irritation.

We claim:

1. A base material composition for dental treatment comprising 1-100 parts by weight of alumina cement powder for curing the composition by hydration of said alumina cement, 1-50 parts by weight of calcium type powder hardener, and 1-20 parts by weight of hardening retarder capable of restraining dispersion of calcium ion, said composition further characterized in that said composition is weakly alkaline and contains free calcium ions.

2. A composition according to claim 1, wherein said calcium type power hardener is used in the amount of about 20 parts by weight.

3. A composition according to claim 1 or 2 wherein said composition is a powder-liquid type composition comprising a mixed powder containing at least alumina cement powder and calcium type powder hardener, and a liquid having at least a hardening retarder dissolved or dispersed therein.

4. A composition according to claim 3 wherein said composition uses a hardening retarder one or a combination thereof selected from the group consisting of polyvinyl alcohol, polyvinylpyrolidone, gum arabic, acrylic acid, glycerine, sodium metasilicate, low-molecular fatty acid, and a hydrophobic natural resin.

5. A composition according to claim 3, further containing titanium oxide powder or aluminum oxide powder as a strength-increasing filler.

6. A composition according to claim 3, further containing an iodoform or poraformaldehyde as an antiseptic.

7. A composition according to claim 3, further containing a suitable contrast medium and an anti-inflammatory agent.

8. A composition according to claim 1 or 2, wherein said composition is a powder-paste type composition comprising powder containing at least alumina cement powder, and a paste containing at least a calcium type powder hardener and a hardening retarder.

9. A composition according to claim 8 wherein said composition uses as a hardening retarder one or a combination thereof selected from the group consisting of polyvinyl alcohol, polyvinylpyrolidone, gum arabic, acrylic acid, glycerine, sodium metasilicate, low-molecular fatty acid, and a hydrophobic natural resin.

10. A composition according to claim 8, further containing titanium oxide powder or aluminum oxide powder as a strength-increasing filler.

11. A composition according to claim 8, further containing an iodoform or poraformaldehyde as an antiseptic.

12. A composition according to claim 8, further containing a suitable contrast medium and an anti-inflammatory agent.

13. A composition according to claim 1 or 2, wherein said composition is a paste-liquid type composition comprising a paste containing at least alumina cement powder and calcium type powder hardener, and a liquid having hardening retainer dissolved or dispersed therein.

14. A composition according to claim 13 wherein said composition uses as a hardening retarder one or a combination thereof selected from the group consisting of polyvinyl alcohol, polyvinylpyrolidone, gum arabic, acrylic acid, glycerine, sodium metasilicate, low-molecular fatty acid, and a hydrophobic natural resin.

15. A composition according to claim 13, further containing titanium oxide powder or aluminum oxide powder as a strength-increasing filler.

16. A composition according to claim 13 further containing an idoform or poraformaldehyde as an antiseptic.

17. A composition according to claim 13, further containing a suitable contrast medium and an anti-inflammatory agent.

18. A composition according to claim 1 or 2, wherein said composition is a paste-paste type composition comprising a paste containing at least alumina cement powder and a paste containing at least calcium type powder hardener and a hardening retarder.

19. A composition according to claim 18 wherein said composition uses as a hardening retarder one or a combination thereof selected from the group consisting of polyvinyl alcohol, polyvinylpyrolidone, gum arabic, acrylic acid, glycerine, sodium metasilicate, low-molecular fatty acid, and a hydrophobic natural resin.

20. A composition according to claim 18, further containing titanium oxide powder or aluminum oxide powder as a strength-increasing filler.

21. A composition according to claim 18 further containing an iodoform or poraformaldehyde as an antiseptic.

22. A composition according to claim 18, further containing a suitable contrast medium and an anti-inflammatory agent.

23. A composition according to claim 1 or 2, wherein said composition uses as a hardening retarder one or a combination thereof selected from the group consisting of polyvinyl alcohol, polyvinylpyrolidone, gum arabic, acrylic acid, glycerine, sodium metasilicate, low-molecular fatty acid, and a hydrophobic natural resin.

24. A composition according to claim 23, further containing titanium oxide powder or aluminum oxide powder as a strength-increasing filler.

25. A composition according to claim 23 further containing an iodoform or poraformaldehyde as an antiseptic.

26. A composition according to claim 23, further containing a suitable contrast medium and an anti-inflammatory agent.

27. A compsition according to claim 1 or 2, further containing titanium oxide powder or aluminum oxide powder as a strength-increasing filler.

28. A composition according to claim 27 further containing an iodoform or poraformaldehyde as an antiseptic.

29. A composition according to claim 27 further containing a suitable contrast medium and an anti-inflammatory agent.

30. A composition according to claim 1 or 2, further containing an iodoform or poraformaldehyde as an antiseptic.

31. A composition according to claim 1 or 2 further containing a suitable contrast medium and an anti-inflammatory agent.

32. A composition according to claim 30, further containing a suitable contrast medium and an anti-inflammatory agent.

* * * * *